(12) United States Patent
Coupard et al.

(10) Patent No.: US 12,210,010 B2
(45) Date of Patent: Jan. 28, 2025

(54) ANALYSIS DEVICE FOR DETECTING SOLID PARTICLES IN A LUBRICANT

(71) Applicant: SAFRAN AIRCRAFT ENGINES, Paris (FR)

(72) Inventors: Josselin Xavier Coupard, Moissy-Cramayel (FR); Alméric Pierre Louis Garnier, Moissy-Cramayel (FR); François Maurice Marcel Demaison, Moissy-Cramayel (FR); Franck Serge Jacques Liotte, Moissy-Cramayel (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 209 days.

(21) Appl. No.: 17/995,838

(22) PCT Filed: Apr. 8, 2021

(86) PCT No.: PCT/FR2021/050625
§ 371 (c)(1),
(2) Date: Oct. 7, 2022

(87) PCT Pub. No.: WO2021/205125
PCT Pub. Date: Oct. 14, 2021

(65) Prior Publication Data
US 2023/0152298 A1 May 18, 2023

(30) Foreign Application Priority Data
Apr. 8, 2020 (FR) ........................ 2003537

(51) Int. Cl.
*G01N 33/28* (2006.01)
*G01N 1/10* (2006.01)
(Continued)

(52) U.S. Cl.
CPC ....... *G01N 33/2858* (2013.01); *G01N 1/2035* (2013.01); *G01N 15/0656* (2013.01);
(Continued)

(58) Field of Classification Search
USPC ........................................... 324/204
See application file for complete search history.

(56) References Cited

U.S. PATENT DOCUMENTS

| 3,432,750 A | 3/1969 | Botstiber |
| 4,657,671 A * | 4/1987 | Botstiber ............. B01D 29/117 |
| | | 210/111 |

(Continued)

FOREIGN PATENT DOCUMENTS

| DE | 102007019064 B3 | 8/2008 |
| EP | 3363518 A1 | 8/2018 |
| FR | 2927401 A1 | 8/2009 |

OTHER PUBLICATIONS

International Search Report issued in PCT/FR2021/050625 on Jul. 6, 2021 (9 pages).
(Continued)

*Primary Examiner* — Farhana A Hoque
(74) *Attorney, Agent, or Firm* — Bookoff McAndrews, PLLC

(57) ABSTRACT

Analysis device for detecting solid particles in suspension in a lubricant, the analysis device comprising one or more ferromagnetic solid particle sensors, one or more other sensors able to detect non-ferromagnetic solid particles, and one or more magnets. The ferromagnetic solid particle sensors are offset in a direction perpendicular to a main direction of flow of the lubricant in relation to the other sensors, and the magnets are arranged so as to attract
(Continued)

ferromagnetic solid particles towards the sensors of ferromagnetic solid particles by drawing them away from the other sensors.

17 Claims, 4 Drawing Sheets

(51) Int. Cl.
    *G01N 1/20*         (2006.01)
    *G01N 15/00*       (2024.01)
    *G01N 15/06*       (2024.01)

(52) U.S. Cl.
    CPC ................ *G01N 2001/1025* (2013.01); *G01N 2001/205* (2013.01); *G01N 2015/0053* (2013.01)

(56) References Cited

U.S. PATENT DOCUMENTS

| | | |
|---|---|---|
| 5,604,441 A | 2/1997 | Freese et al. |
| 2002/0178780 A1 | 12/2002 | Van Mullekom et al. |
| 2011/0214511 A1 | 9/2011 | Fjerdingstad |
| 2015/0108047 A1 | 4/2015 | Rem et al. |
| 2016/0131575 A1* | 5/2016 | Brekke .............. G01N 33/2847 356/70 |
| 2016/0313237 A1 | 10/2016 | Young et al. |
| 2016/0370275 A1 | 12/2016 | Weiser |

OTHER PUBLICATIONS

Written Opinion issued in PCT/FR2021/050625 on Jun. 28, 2021 (8 pages).

Search Report issued in FR 2003537 on Nov. 23, 2020 (2 pages).

* cited by examiner

[Fig. 1]
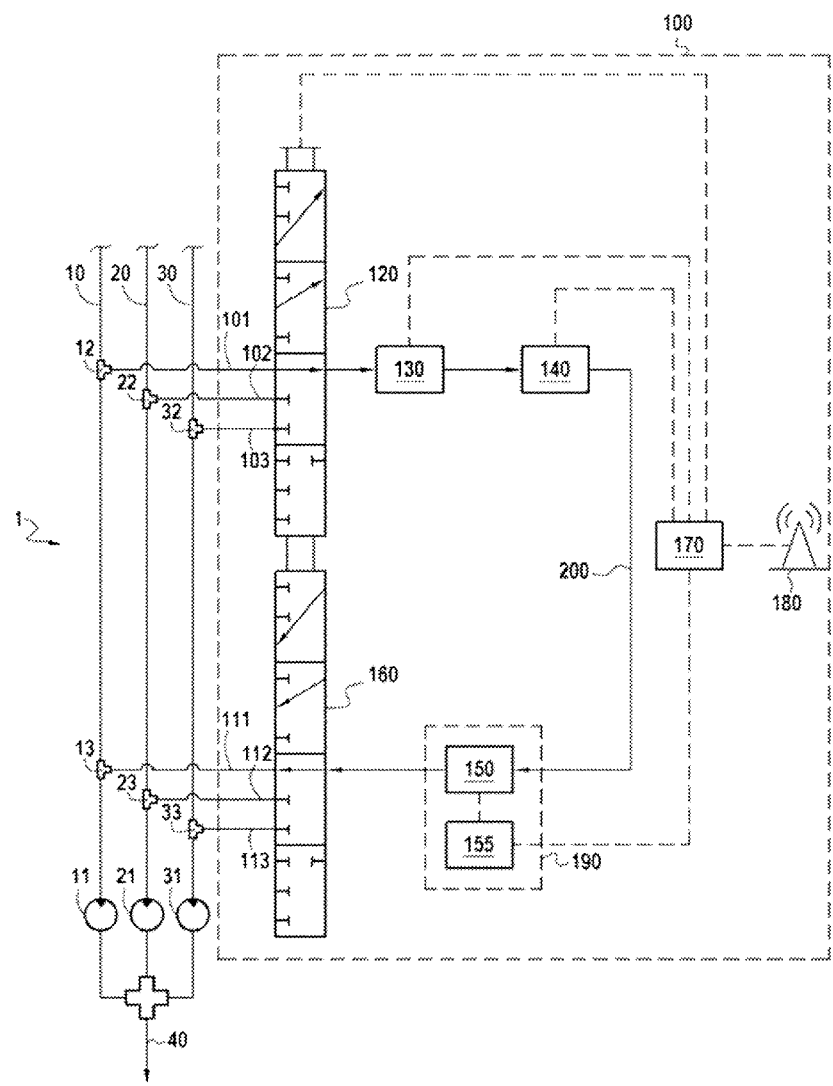

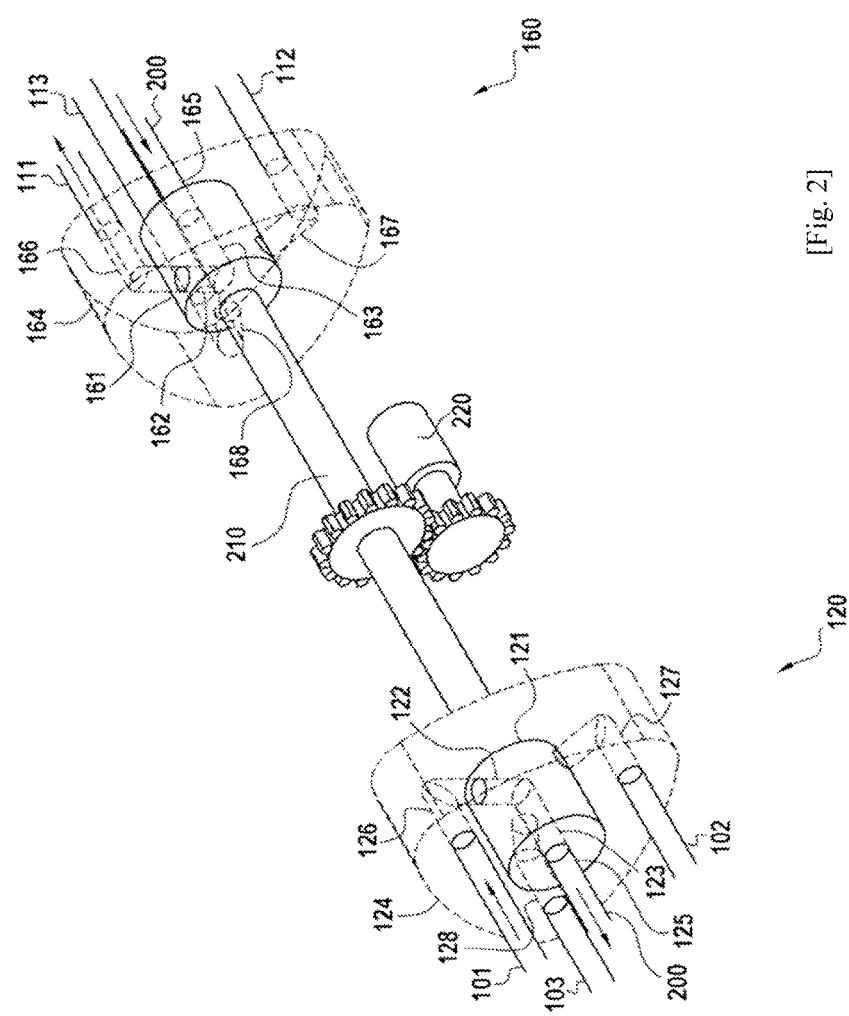
[Fig. 2]

[Fig. 3A]
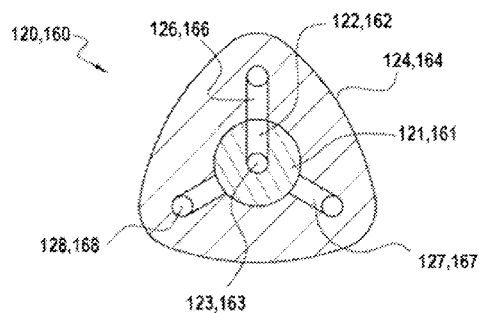
[Fig. 3B]
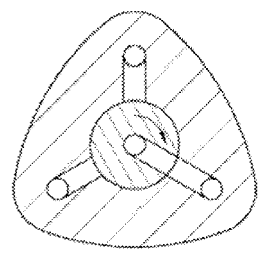
[Fig. 3C]
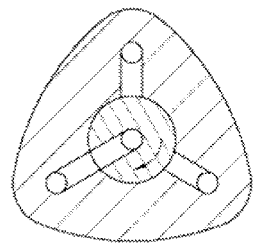

[Fig. 3D]
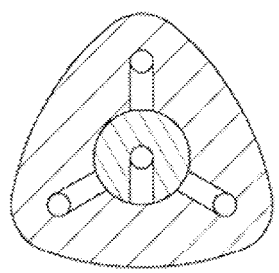
[Fig. 4]
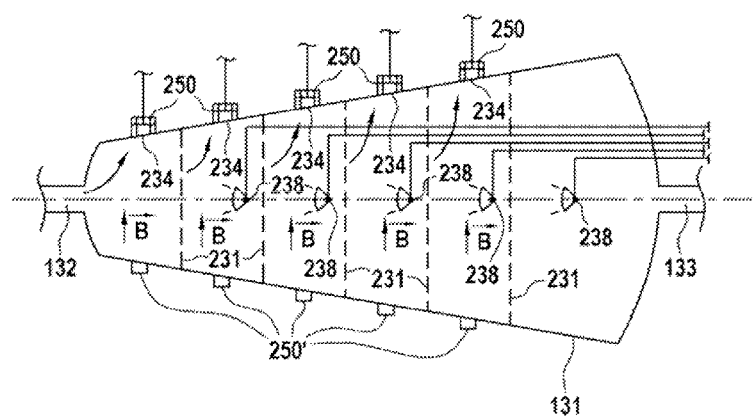

ANALYSIS DEVICE FOR DETECTING SOLID PARTICLES IN A LUBRICANT

CROSS-REFERENCE TO RELATED APPLICATION(S)

This patent application is the U.S. National Stage entry under 35 U.S.C. § 371 of International Patent Application No. PCT/FR2021/050625, filed on Apr. 8, 2021, which claims the benefit of priority to French Patent Application No. 2003537, filed on Apr. 8, 2020.

TECHNICAL FIELD

The present disclosure concerns the field of lubricant monitoring in machines, and more specifically an analysis device for detecting solid particles in suspension in a lubricant.

PRIOR ART

To reduce operating costs, it is ascertained throughout the entire mechanical sector that lubricant maintenance and change times are being extended. In the more specific field of combustion engines and in particular gas turbine engines such as those used in aeronautics, a gradual reduction is observed in lubricant consumption leading to longer use of a lubricant before it is changed.

With this reduction in the frequency of lubricant change, there is also a reduction in the opportunities to observe and/or analyze the quality of a lubricant at each oil change. Yet this observation and analysis of used oil allows the detection not only of unexpected changes in the properties of the lubricant itself, but also, through these properties of the used oil, such as the presence of fuel or filings in the lubricant, of malfunctions in the lubricated machine.

It is already known, see for example French patent application having publication number FR 2 927 401 A1, to integrate indwelling sensors and in particular sensors of metal particles in the lubrication circuit. American U.S. Pat. Nos. 4,657,671 A, 5,604,441 A and 3,432,750 disclose devices combining sensors of ferromagnetic and non-ferromagnetic particles for separate detection thereof.

However, despite the presence of such sensors, the simultaneous detection of different types of solid particles in suspension can still remain desirable through better distinguishing therebetween.

DESCRIPTION OF THE INVENTION

A first aspect of the invention concerns an analysis device for detecting solid particles in suspension in a lubricant. The analysis device may comprise one or more ferromagnetic solid particle sensors, and one or more other sensors able to detect non-ferromagnetic solid particles. By "non-ferromagnetic solid particle" in this context any solid particle can be understood which has a magnetic susceptibility equal to or less than $10^4$ for example. These other sensors can be offset in a direction perpendicular to a main direction of flow of the lubricant with respect to the ferromagnetic solid particle sensors, and the analysis device may further comprise one or more magnets arranged so as to attract the ferromagnetic solid particles towards the ferromagnetic solid particle sensors by drawing them away from the other sensors. The ferromagnetic solid particle sensors can in particular be inductive sensors, wherein each may comprise a winding oriented in a direction perpendicular to the main direction of flow of the lubricant, and the sensors of non-ferromagnetic solid particles can be optical and/or acoustic sensors and in particular be configured to detect the wavelength and/or light intensity reflected by non-ferromagnetic solid particles. Each of the ferromagnetic solid particle sensors can in particular be directional and oriented to detect ferromagnetic solid particles in a direction perpendicular to the main direction of flow of the lubricant, and each of said other sensors can in particular be directional and oriented to detect non-ferromagnetic solid particles in a direction parallel to the main direction of flow of the lubricant.

By means of this arrangement, the ferromagnetic and non-ferromagnetic solid particles in suspension in the lubricant can be detected separately. This characterization of the solid particles in suspension in the lubricant therefore allows better diagnosis of their origin and more accurate prediction of the consequences of this contamination of the lubricant.

In a second aspect, the analysis device may further comprise one or more grids arranged crosswise to the main direction of flow of the lubricant, to separate per size the solid particles in suspension in the lubricant. Each of said other sensors can therefore be arranged to detect non-ferromagnetic solid particles on each of the grids. For this purpose, each of said other sensors can particularly be arranged facing a corresponding grid from among said grids. The grids may particularly comprise at least one first grid and a second grid arranged downstream of the first grid in the main direction of flow of the lubricant, the second grid being finer than the first grid so as to separate solid particles of smaller size. It is therefore possible, in addition to separation between solid ferromagnetic and non-ferromagnetic particles, to obtain separation per size allowing even better characterization of all the solid particles in suspension in the lubricant.

A third aspect of this disclosure concerns a lubricant monitoring system comprising the analysis device of the first aspect, one or more inlet connections and one or more outlet connections. Each of the inlet connections is able to be to connected, in particular releasably, to a lubricant circuit to allow the entry of lubricant from the lubricant circuit into the analysis devices, and each of the outlet connections is connectable, in particular releasably, to the lubricant circuit so as to allow return of the lubricant through the analysis devices towards the lubricant circuit.

By means of these characteristics, it is possible to install this lubricant monitoring system on a lubricant circuit for continuous or intermittent monitoring of one of more parameters of the lubricant over an operating period of the lubricant circuit. In particular, this installation can be temporary.

If the lubricant monitoring system comprises several of said inlet connections, it may further comprise a selective inlet valve to place said inlet connections selectively in fluid communication with the analysis devices. It is thus possible alternately to select several lubricant sample points to be monitored, thereby allowing the identification of specific sources of lubricant degradation within the circuit.

Additionally, when the lubricant monitoring system further comprises several of said outlet connections, it may also comprise a selective outlet valve to place said outlet connections selectively in fluid communication with the analysis devices. The selective inlet valve and selective outlet valve can be coupled together to synchronize their selections and therefore return the lubricant back towards the same branch of the lubrication circuit on which it was sampled. The selective inlet valve and/or selective outlet valve may comprise a rotative valve body e.g. in cylinder form to allow selection of an inlet connection and/or outlet connection by rotating this valve body. However, alternative shapes of selective valves e.g. slide-type can also be considered.

To ensure operation of the sensors, and even of other parts of the lubricant monitoring system, they may further comprise an electric powering device. This electric powering device may particularly comprise a turbine able to be actuated by lubricant flow through the lubricant monitoring system and/or a thermocouple thermally interposed between the lubricant and a heat sink, to ensure independent electric powering of the lubricant monitoring system by drawing on the thermal or mechanical energy of the lubricant itself. However, it could also be envisaged that the electric powering device comprises a power storage device alternatively to or in combination with said turbine and/or thermocouple.

The lubricant monitoring system may also comprise a communication device connected to the analysis device to transmit data captured by the sensors to a user and/or external device.

Additionally, the lubricant monitoring system may further comprise a second analysis device including one or more lubricant quality sensors such an optical sensor, sensor of electrical conductivity, temperature sensor and/or viscosity sensor.

BRIEF DESCRIPTION OF THE DRAWINGS

The invention will be clearly understood and the advantages thereof will become better apparent on reading the following detailed description of embodiments illustrated as nonlimiting examples. The description refers to the appended drawings in which:

FIG. 1 is a partial schematic illustration of a lubricant circuit with a lubricant monitoring system according to one embodiment.

FIG. 2 is an illustration in perspective of a selective inlet valve and outlet valve having coupled rotative bodies, of the monitoring system in FIG. 1.

FIG. 3A is a cross-sectional view along plane III-III of the selective valve in FIG. 2 at a first position.

FIG. 3B is a cross-sectional view along plane III-III of the selective valve in FIG. 2 at a second position.

FIG. 3C is a cross-sectional view along plane III-III of the selective valve in FIG. 2 at a third position.

FIG. 3D is a cross-sectional view along plane III-III of the selective valve in FIG. 2 at a fourth position.

FIG. 4 is a schematic illustration of an analysis device belonging to the monitoring system in FIG. 1.

DESCRIPTION OF EMBODIMENTS

FIG. 1 schematically illustrates part of a lubricant circuit 1 able to be used to lubricate a machine, and in particular a turbomachine such as a turbojet aeroengine. However, other applications in particular aeronautic, automotive, marine or railway applications can also be envisaged. As illustrated in FIG. 1, this lubricant circuit 1 may comprise a plurality of branches 10, 20, 30 which may derive from different members or zones of the lubricated machine and meet up as illustrated in a common line 40 downstream of corresponding pumps 11, 21, 31. Each of the branches 10, 20, 30, as illustrated, may comprise an upstream branch 12, 22, 32 and downstream branch 13, 23, 33 allowing connection thereof to the lubricant monitoring system 100 parallel to branches 10, 20, 30. The upstream branches 12, 22, 32 and downstream branches 13, 23, 33 can all be arranged upstream of the corresponding pumps 11, 21, 31. For example, they can substitute for orifices conventionally used to insert magnetic sensors of metal particles in the lubricant circuit 1. Plugs, not illustrated, are able to shut off these upstream 12, 22, 32 and downstream 13, 23, 33 branches when the lubricant monitoring system 100 is not connected to the lubricant circuit 1.

The lubricant monitoring system 100 may comprise an inlet connection 101, 102, 103 and outlet connection 111, 112, 113 for each of the branches 10, 20, 30 of the lubricant circuit 1. Each of the inlet connections 101, 102, 103 can be releasably connected to one from among the plurality of upstream branches 12, 22, 32. Similarly, each of the outlet connections 111, 112, 113 can be releasably connected to one from among the plurality of downstream branches 13, 23, 33.

Although, in the illustrated example, the lubricant circuit 1 comprises three branches 10, 20, 30 and the lubricant monitoring system 100 therefore has the same number of inlet connections 101, 102, 103 and outlet connections 111, 112, 113, it can be envisaged to have a different number of branches and hence of corresponding inlet and outlet connections. It can also be envisaged to have a greater number of inlet connections than outlet connections if, for example, at least some of the branches meet up at a confluence upstream of the pumps, so that an outlet connection of the lubricant monitoring system is connectable to the lubricant circuit between the confluence and downstream pump, or if a single outlet connection is connected to the common line 40 downstream of the pumps 11, 21, 31, which would additionally require the integration of a pump in the lubricant monitoring system 100.

Between the inlet connections 101, 102, 103 and outlet connections 111, 112, 113, the lubricant monitoring system 100 may comprise a selective inlet valve 120, a first analysis device 130, a second analysis device 140, a power extraction device 150, and a selective outlet valve 160 in fluid communication in series. Additionally, the lubricant monitoring system 100 may comprise a control unit 170, a communication device 180 and an electric powering device 190 which may comprise the power extraction device 150.

The selective inlet valve 120 can be configured to selectively place each of the inlet connections 101, 102, 103 in fluid communication with a line 200 passing through the analysis devices 130, 140 and even the power extraction device 150 downstream. The selective inlet valve 120 can also be configured to isolate line 200 from the assembly of inlet connections 101, 102, 103 so that the lubricant may continue to circulate on each of the branches 10, 20, 30 of the lubricant circuit 1 without being taken for sampling. Similarly, the selective outlet valve 160 can be configured to selectively place line 200 downstream of the analysis devices, even downstream of the power extraction device 150, in fluid communication with each of the outlet connections 111, 112, 113, or to isolate the same from the assembly of outlet connections 111, 112, 113. The selective inlet 120 and outlet 160 valves may particularly be in the form of valves with rotative bodies, preferably coupled together for example mechanically as illustrated in FIG. 2.

As can be seen in FIGS. 2 and 3A to 3C, the rotative valve bodies 121, 161 of the selective inlet valve 120 and selective outlet valve 160 respectively, may each have a radial through-hole 122, 162 and an axial through-hole 123, 163 in fluid communication with each other. The radial through-hole 122, 162 can open onto a peripheral surface of the rotative valve body 121, 161, while the axial through-hole 123, 163 can open onto a front surface of the rotative valve body 121, 161. The selective inlet valve 120 and selective outlet valve 160 may further each comprise a valve casing 124, 164 with a central orifice 125, 165 which may lie opposite the axial through-hole 123, 163, and peripheral orifices 126, 127, 128, 166, 167, 168.

The radial orifices 126, 127, 128 of the valve casing 124 of the selective inlet valve 120 can each be in fluid communication with one of the inlet connections 101, 102, 103. The central orifice 125 of the valve casing 124 can be in fluid communication with line 200. The radial through-hole 122 of the rotative valve body 121 of the selective inlet valve 120 can be selectively placed facing each of these peripheral orifices 126, 127, 128 via relative rotation of the rotative valve body 121 in relation to the valve casing 124 about its central axis X, so as selectively to place in fluid communication each of the inlet connections 101, 102, 103 with line 200 as illustrated in FIGS. 3A to 3C. The radial through-hole 122 of the rotative valve body 121 of the selective inlet valve 120 is also able to turn towards an intermediate position as illustrated in FIG. 3D to isolate the line 200 from the three inlet connections 101, 102, 103.

Analogously, the radial orifices 166, 167, 168 of the valve casing 164 of the selective outlet valve 160 can each be placed in fluid communication with one of the outlet connections 111, 112, 113. The central orifice 165 of the valve casing 164 can be in fluid communication with the line 200. The radial through-hole 162 of the rotative valve body 161 of the selective outlet valve 160 can be selectively placed facing each of these peripheral orifices 166, 167, 168 via relative rotation of the rotative valve body 161 in relation to the valve casing 164 about its central axis X, to selectively place in fluid communication each of the outlet connections 111, 112, 113 with the line 200, or to isolate this line 200 from the three outlet connections 111, 112, 113.

As illustrated in FIG. 2, the rotative valve bodies 121, 161 can be mechanically coupled via a common rotating shaft 210 which in turn can be mechanically coupled to an actuation device 220 such as a stepper motor electrically connected to the control unit 170 for electrical powering and control thereof. Therefore, the respective selections of the selective inlet valve 120 and selective outlet valve 160 can be synchronized. However, the selective inlet valve 120 and selective outlet valve 160 can be configured differently to the illustrated rotating configuration, and can be in the form of slide valves for example.

As illustrated in FIG. 4, the first analysis device 130 can be a device analyzing solid particles in suspension in the lubricant. It may comprise a casing 131 with a succession of mesh grids 231 that are increasingly finer between the inlet 132 and outlet 133 thereof, to separate the solid particles per size. For example, a first grid 231 can have a mesh size of 8 mm², a second grid 231 downstream of the first grid 231 can have a mesh size of 4 mm², a third grid 231 downstream of the second grid 231 can have a mesh size of 1 mm², a fourth grid 231 downstream of the third grid 231 can have a mesh size of 0.1 mm² and a fifth grid 231 downstream of the fourth grid 231 can have a mesh size of 0.02 mm² so that each retains particles of greater cross-section than the corresponding mesh size. The mesh size of the successive grids could alternatively follow inverse square progression following formula $A_i=A_1/i^2$, where i is the position of the grid from upstream to downstream and $A_i$ is the mesh size of the respective grid. Alternative means for separating solid particles per size e.g. centrifugation can also be envisaged.

The first analysis device 130 may also comprise ferromagnetic particle sensors 234, lying flush for example on the walls of the casing 131, upstream of each grid 231, to detect ferromagnetic particles of different corresponding sizes. These ferromagnetic particle sensors 234 can be inductive sensors for example and notably each comprise a winding (not illustrated) having an axis that can be oriented perpendicular to the main direction of flow of the lubricant between the inlet 132 and outlet 133 of the first analysis device 130, to detect ferromagnetic particles in the axis of the winding via variation of a magnetic field passing through the winding. Therefore, each sensor 234 can be configured, with at least 65% efficacy for example, to detect a ferromagnetic particle of at least 0.130 mg for example with a length-width size ratio of up to 20:1 for example.

One or more magnets 250 can be arranged on the periphery of the casing 131 to attract ferromagnetic particles towards the ferromagnetic particle sensors 234. Each of these magnets 250 can particularly be arranged coaxial to the winding of one of the ferromagnetic particle sensors 234, so as not only to attract the ferromagnetic particles towards the corresponding sensor 234 but also to provide the magnetic field of which the variation will allow detection thereof by the sensor 234. Each magnet 250 can be a permanent magnet or alternatively an electromagnet with a winding which can then lie coaxial to that of the corresponding sensor 234. Optionally, another magnet 250' oriented along the same polarity can be arranged facing each of the magnets 250 on an opposite wall of the casing 230. Magnets 250 can have different intensities and in particular intensities increasing in the direction of flow of the lubricant from the inlet 132 to the outlet 133 of the first analysis device 130, to compensate for the decreasing size of the ferromagnetic solid particles passing through the successive grids 231. To obtain these different intensities, they can be electromagnets for example having windings with a different number of turns powered by the same voltage. It can also be envisaged to control the powering voltage of each electromagnet, jointly or separately, and in particular as a function of the lubricant flow passing through the first analysis device 130. The powering voltage of each electromagnet can be between 0 and 24 V for example, preferably between 120 mV and 4 V.

The first analysis device 130 may also comprise other particle sensors 238 which can be arranged for example in a central zone of the casing 131 facing each grid 231, to detect non-ferromagnetic particles of different corresponding sizes retained on each grid 231. These other particle sensors 238 can particularly be acoustic and/or optical sensors. In particular, they can be optical sensors to perform reflectometry, configured to detect a wavelength and/or light intensity reflected by the non-ferromagnetic solid particles, and thereby allow a distinction to be made between different types of non-ferromagnetic solid particles. The light reflected by the non-ferromagnetic solid particles can derive from one or more sources, for example light-emitting diodes integrated in each sensor 238 or external thereto. To allow illumination of non-ferromagnetic solid particles through the lubricant, the light emitted by these sources and captured by the sensors 238 can be restricted to some spectral bands and in particular the visible spectrum. Strain sensors (not illustrated) can also be coupled with each grid 231 and contribute towards measuring the quantity of solid particles on each of the grids 231.

By offsetting the ferromagnetic particle sensors 234 perpendicularly to the main direction of flow of the lubricant, these possibly being arranged on the periphery of the casing 131 in relation to the other sensors 238 positioned in the central zone of the casing 131, and by means of the arrangement of the magnets 250 to attract ferromagnetic particles towards the sensors 234 by drawing them away from the other sensors 238, it is possible to prevent the detection of ferromagnetic solid particles by these other sensors 238 and thereby separately detect the two types of solid particles. Each of the sensors 234 and 238 can be connected to the control unit 170 to transmit thereto the detection of these particles.

The second analysis device 140 may comprise one or more other sensors such as an electrical conductivity sensor, optical sensor to capture the colour and/or turbidity of the lubricant, a viscosity sensor, a thermometer, a manometer, a vibration sensor and/or an acoustic sensor. Each of these sensors of the second analysis device 140 may also be connected to the control unit 170 to transmit thereto the data they have captured.

The power extraction device 150 can be a turbine able to be pulsed by the lubricant flow through line 200, and coupled to an electric generator or a thermocouple able to produce electricity from the thermal gradient between the lubricant circulating through line 200 and a heat sink e.g. a radiator, an airstream and/or a fuel circuit. This power extraction device 150 can be electrically connected to a power storage device 155 which can be a battery for example, a capacitor and/or flywheel to form the electric powering device 190. This electric powering device 190 can be electrically connected to other members of the lubricant monitoring system 100 so as to ensure powering thereof, optionally even independently, However, alternatively, or in addition to this electric powering device 190, an external electrical connection can also be envisaged. Additionally, it can also be envisaged that the electric powering device 190 does not comprise a power extraction device, and ensures the electrical powering of the lubricant monitoring system 100 solely from the power previously stored in the power storage device 155, or alternatively it does not comprise a power storage device and ensures the electrical powering of the lubricant monitoring system from the power drawn by the power extraction device 150 from the flow of lubricant passing through it.

The control unit 170 can be an electronic computer, optionally programmable. It can therefore be integrated into an integrated circuit or microprocessor and incorporate a data storage member. Finally, the control unit 170 is connected to a communication device 180 to transmit the data captured by the different sensors of the analysis devices 130, 140, and/or the results of their analysis by the control unit, to external systems and/or to users. This communication device 180, as illustrated, can be a wireless communication device, but also a simple electrical and/or optical connector for data transmission. The control unit 170 can also be configured to place the lubricant monitoring system 100 in inactive mode, in particular by actuating the selective inlet 120 and outlet 160 valves to isolate line 200 from the inlet 101, 102, 103 and outlet 111, 112, 113 connections, for example in the event that the electric powering device 190 is no longer able to provide sufficient electrical power for normal operation of the lubricant monitoring system 100.

To use the lubricant monitoring system 100, it can first be installed by connecting an inlet connection 101, 102, 103 and an outlet connection 111, 112, 113 of the lubricant monitoring system 100 to each of the branches 10, 20, 30 of the lubricant circuit 1 through the respective upstream branch 12, 22, 32 and downstream branch 13, 23, 33, after removing the plugs from the latter.

At a subsequent lubricant monitoring step, some lubricant can be successively diverted from each of the branches 10, 20, 30 through line 200 of the lubricant monitoring system 100 by selecting each corresponding inlet connection 101, 102, 103 and outlet connection 111, 112, 113 with the selective inlet valve 120 and selective outlet valve 160 optionally controlled by the control unit 170. The lubricant circulating through line 200 can therefore pass through the first analysis device 130 of which the different sensors can separately detect metal and non-metal solid particles of different sizes, and the second analysis device 140 of which the different sensors can detect the properties of the lubricant such as colour, turbidity, electrical conductivity, viscosity, temperature and/or pressure, as well as possible sounds and/or vibrations. The data captured by the sensors of the analysis devices 130, 140 at this monitoring step can be transmitted to the control unit 170 for processing, analysis, storage and/or transmission via the communication device 180. In addition, at this monitoring step, the electric powering device 190 can electrically power the different other members of the lubricant monitoring system 100 with electrical power drawn by the power extraction device 150 on the lubricant flow passing through it and/or recovered from the power storage device 155.

When it is decided to finalize monitoring of the lubricant, the lubricant monitoring system 100 can be uninstalled by separating each inlet connection 101, 102, 103 and each outlet connection 111, 112, 113 of the lubricant monitoring system 100 from the respective upstream branches 12, 22, 32 and downstream branches 13, 23, 33, and shutting off the latter with the plugs.

Although the present invention has been described with reference to specific examples of embodiment, it is obvious that different modifications and changes can be made to these examples without departing from the general scope of the invention such as defined by the claims. Also, individual characteristics of the different described embodiments can be combined in additional embodiments. The description and drawings must therefore be construed as illustrative rather than restrictive.

The invention claimed is:

1. An analysis device for detecting solid particles in suspension in a lubricant, the analysis device comprising: one or more ferromagnetic solid particle sensors, one or more other sensors able to detect non-ferromagnetic solid particles, these other sensors being offset in a direction perpendicular to a main direction of flow of the lubricant in relation to the ferromagnetic solid particle sensors, and one or more magnets arranged so as to attract the ferromagnetic solid particles towards the ferromagnetic solid particle sensors by drawing them away from the other sensors.

2. The analysis device according to claim 1, wherein each of the ferromagnetic solid particle sensors is directional and oriented to detect ferromagnetic solid particles in a direction perpendicular to the main direction of flow of the lubricant.

3. The analysis device according to claim 1, wherein each of the other sensors is directional and oriented to detect non-ferromagnetic solid particles in a direction parallel to the main direction of flow of the lubricant.

4. The analysis device according to claim 1, further comprising one or more grids arranged crosswise to the main direction of flow of the lubricant, to separate per size the solid particles in suspension in the lubricant.

5. The analysis device according to claim 4, wherein each of said other sensors is arranged to detect non-ferromagnetic solid particles on each of the grids.

6. The analysis device according to claim 4, wherein the grids comprise at least one first grid and a second grid arranged downstream of the first grid in the main direction of flow of the lubricant, the second grid being finer than the first grid so as to separate solid particles of smaller size.

7. The analysis device according to claim 1, wherein the ferromagnetic solid particle sensors are inductive sensors.

8. The analysis device according to claim 7, wherein each ferromagnetic solid particle sensor comprises a winding oriented in a direction perpendicular to the main direction of flow of the lubricant.

9. The analysis device according to claim 1, wherein the other sensors are optical and/or acoustic sensors.

10. The analysis device according to claim 9, wherein each of said other sensors is configured to detect a wavelength and/or light intensity reflected by non-ferromagnetic solid particles.

11. A lubricant monitoring system comprising:

an analysis device according to claim 1, one or more inlet connections each connectable to a lubricant circuit to allow the entry of lubricant from the lubricant circuit into the analysis device, one or more outlet connections each connectable to the lubricant circuit so as to allow return of the lubricant through the analysis device towards the lubricant circuit.

12. The lubricant monitoring system according to claim 11, wherein the inlet connections and outlet connections are releasably connectable to the lubricant circuit.

13. The lubricant monitoring system according to claim 11, comprising several of said inlet connections and a selective inlet valve to place said inlet connections selectively in fluid communication with the analysis devices.

14. The lubricant monitoring system according to claim 13, wherein the selective inlet valve comprises a rotative valve body.

15. The lubricant monitoring system according to claim 13, comprising several of said outlet connections and a selective outlet valve to place said outlet connections selectively in fluid communication with the analysis device.

16. The lubricant monitoring system according to claim 15, wherein the selective inlet valve and selective outlet valve are coupled together.

17. The lubricant monitoring system according to claim 11, comprising a communication device connected to the analysis device.

* * * * *